United States Patent
Bassile

(10) Patent No.: US 8,685,716 B2
(45) Date of Patent: Apr. 1, 2014

(54) COMPOSTING APPARATUS AND METHOD

(75) Inventor: Elias Bassile, Hudson (CA)

(73) Assignee: Great Wall of China Waste Company Inc., Kirkland (CA)

( * ) Notice: Subject to any disclaimer, the term of this patent is extended or adjusted under 35 U.S.C. 154(b) by 293 days.

(21) Appl. No.: 13/104,131

(22) Filed: May 10, 2011

(65) Prior Publication Data

US 2012/0285209 A1    Nov. 15, 2012

(51) Int. Cl.
    *C12M 1/00*      (2006.01)
    *C12M 1/10*      (2006.01)
    *C12M 3/00*      (2006.01)

(52) U.S. Cl.
    CPC . *C12M 1/00* (2013.01); *C12M 1/10* (2013.01); *C12M 3/00* (2013.01)
    USPC .................. 435/290.3; 435/290.1; 435/290.4; 435/290.2; 435/291.7; 435/296.1; 435/298.2

(58) Field of Classification Search
    CPC ............. C12M 1/00; C12M 1/10; C12M 3/00
    USPC .......... 435/290.1, 290.3, 290.4, 290.2, 291.7, 435/298.1, 298.2
    See application file for complete search history.

(56) References Cited

U.S. PATENT DOCUMENTS

| | | | |
|---|---|---|---|
| 2,178,818 A | 11/1939 | Earp-Thomas | |
| 2,639,902 A | 5/1953 | Kuebler | |
| 3,930,799 A * | 1/1976 | Eweson | ..................... 435/290.3 |
| 4,168,915 A * | 9/1979 | Hahn et al. | ..................... 366/105 |
| 4,358,540 A | 11/1982 | Itoh et al. | |
| 5,258,306 A | 11/1993 | Goldfarb | |
| 5,300,438 A * | 4/1994 | Augspurger et al. | ...... 435/290.3 |
| 5,409,831 A | 4/1995 | Wright | |
| 5,427,947 A * | 6/1995 | Dalos | ......................... 435/290.3 |
| 5,597,732 A | 1/1997 | Bryan-Brown | |
| 5,605,834 A | 2/1997 | Eberthson et al. | |
| 5,744,351 A | 4/1998 | Bryan-Brown | |
| 5,766,935 A | 6/1998 | Seagren | |
| 5,846,815 A | 12/1998 | Wright | |
| 5,945,332 A | 8/1999 | Fors | |
| 6,071,740 A | 6/2000 | Kerouac | |
| 6,110,727 A | 8/2000 | Widmer et al. | |
| 7,138,271 B2 * | 11/2006 | Pratte | ......................... 435/290.2 |
| 7,520,457 B1 | 4/2009 | Poitras et al. | |
| 2008/0022739 A1 | 1/2008 | Aswani | |
| 2010/0055775 A1* | 3/2010 | O'Kane | ..................... 435/290.3 |

* cited by examiner

*Primary Examiner* — Nathan Bowers
(74) *Attorney, Agent, or Firm* — Norton Rose Fulbright Canada LLP

(57) ABSTRACT

A composting apparatus and method is described. The apparatus comprises a cylindrical drum which is horizontally rotatably supported. A hopper is disposed at a feed end of the drum for receiving organic waste material in soft or hard form. A material shredding mechanism and a grinding mechanism are rotatably secured in the hopper and driven in counter-rotation for shredding and grinding the organic waste material and feeding it into an inlet opening of the drum. A series of material mixing and conveying vane assemblies are secured spaced-apart inside the drum and define sub-composting compartments therebetween. The material mixing and conveying vane assemblies have a plurality of vanes secured in spaced-apart relationship and project interiorly towards a central longitudinal axis of the drum and are oriented at a common angle to mix, further shred and displace shredded and ground material from the inlet opening towards the rear discharge end of the drum. The gases escaping from the drum are vented from an enclosure of the composting apparatus and the material inside the drum is discharged by suction.

14 Claims, 8 Drawing Sheets

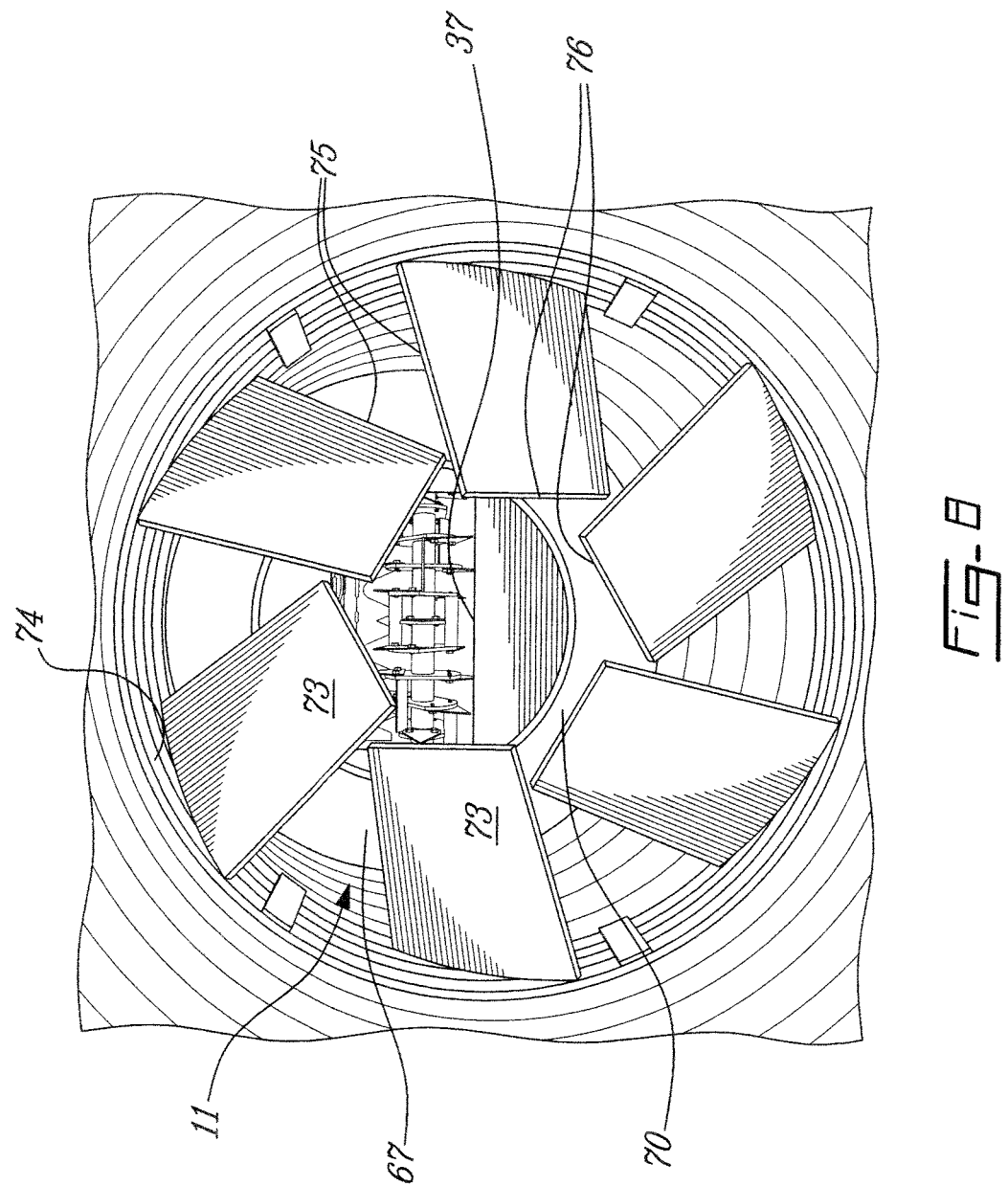

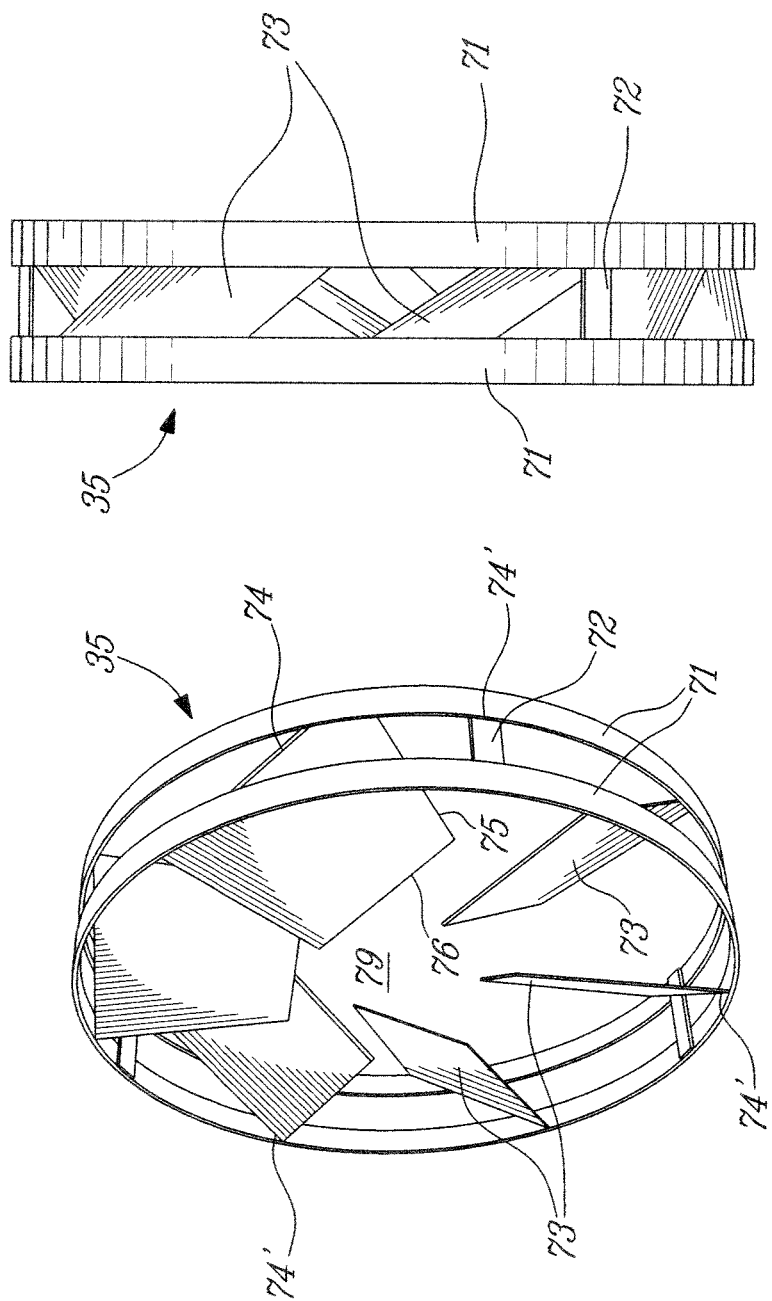

COMPOSTING APPARATUS AND METHOD

TECHNICAL FIELD

The present invention relates to a composting apparatus and method for the degradation of organic waste in soft or hard form.

BACKGROUND ART

The present invention utilizes a horizontal rotating drum in which organic waste material in hard or soft form is shredded and ground in a hopper before being introduced in an inlet opening of the drum which is constantly in rotation. Oxygen in the air surroundings of the drum is introduced therein through the hopper during normal use of the composter apparatus and surrounding air in an enclosure for the composter is exhausted. Such horizontal drum composters are known in the art but these known composters have several disadvantages in that many of these utilize screens to divide the drum into sub-composting compartments and the drums are oriented at an angle whereby the compost material can move from an inlet end to an outlet end during rotation of the drum. For the material to move through the compartments, it needs to decompose to pass through the screens and often the inlet end of the drum will clog up with material which backs up to the inlet end for the reason that the decomposition has not sufficiently taken place and cannot pass through the screens and backs up. The material also clogs the screens and requires constant servicing to unclog. Accordingly, these composters have not proven to be efficient.

Other rotating drum systems work with forced air throughflow and again are provided with sieves against which material to be treated is forced by suitable means such as screw conveyors. Many of these sieve walls have a large central opening. The sieves also have a common mesh size and this implies that no large size particles are present at the discharge side of the drum. Again, drum constructions have been found to be expensive to construct and require constant maintenance and repair due to sieve malfunction.

The treatment of organic waste material also often requires several manipulations for the disposal thereof. For example, organic waste is usually collected in large establishments such as food processing plants or large grocery stores where the organic waste is placed in special bins or bags and is picked up by transparent vehicles to be brought to a disposal site, such as a landfill where it may be buried. The cost of transporting and disposing large volumes of organic waste has escalated in recent years due to increase in labour cost and transportation costs. Such organic waste also is not put to valuable use such as for the fertilization of soil whereby to be recycled into nature. When organic waste is used as landfills, it is slowly decomposed and if such is buried while being contained in plastic bags, the decomposition will take much longer and contamination results due to the use of plastics material. The odors released from these sites are also a nuisance to the environment.

It is known to dispose organic waste from food handling facilities where the organic waste is firstly ground in a mill and mixed with water before being discharged into a storage tank which is buried into the ground next to the facility for storage purpose. Periodically a vehicle having a suction hose removes the waste from the storage tank and transports it to a disposal site where the waste material is tilled into the soil for decomposition by soil organisms. Such disposal systems are used in commercial applications.

SUMMARY OF INVENTION

It is a feature of the present invention to provide a composting apparatus and method which substantially overcomes the above-mentioned disadvantages of the prior art.

Another feature of the present invention is to provide a compositing apparatus which is compact, easy to use and empty, economical to construct, requires very little maintenance and which can compost soft and hard organic materials.

Another feature of the present invention is to provide a composting apparatus which may be constructed in different sizes to treat domestic organic material from multi-residence buildings, grocery stores and food processing plants of all sorts such, as meat or produce handling plants.

Another feature of the present invention is to provide a composting apparatus which uses a rotatable cylindrical drum, the inner digestion chamber of which can be substantially evacuated by suction.

Another feature of the present invention is to provide a composting apparatus which is totally integrated and which is transportable and can be moved to different sites.

Another feature of the present invention is to provide an improved composting method for composting organic waste material in soft and hard form.

According to the above features, from a broad aspect, the present invention provides a composting apparatus which comprises a cylindrical drum rotatably supported along a central longitudinal axis thereof. A drive means is provided for rotating the drum about the longitudinal axis. A hopper is integrated with the drum and provided at a feed end of the drum for receiving organic waste material. A material shredding mechanism and grinding mechanism is rotatably secured in the hopper for shredding and grinding the organic waste material and feeding same to an inlet opening of the drum. Two or more material mixing and conveying vane assemblies are secured in spaced-apart relationship in the drum and rotatable therewith. The material mixing and conveying vane assemblies define sub-composting compartments therebetween. One of the material mixing and conveying vane assemblies is positioned adjacent the inlet opening. Each of the material mixing and conveying vane assemblies have a cylindrical support securable to an inner face of the drum and a plurality of vanes are secured in spaced-apart relationship to the cylindrical support and project interiorly towards the central longitudinal axis of the drum and oriented at a common angle to mix, and continue to shred, and displace shredded and ground material from the inlet opening towards the rear end of the drum. Means is provided to vent the enclosure. Discharge means is provided to discharge the material from the drum.

According to a further broad aspect of the present invention there is provided a method of composting organic waste material and which comprises the steps of feeding the waste material in a hopper associated with a feed end of a cylindrical composting drum and wherein the waste material is directed for shredding and grounding by a combination of a toothed feeder shaft having a series of cutting teeth intermeshed with a plurality of cutting blades secured to a chopper shaft. The feeding shaft and chopper shaft are driven in counter-rotation. The shredded and ground organic waste material is ejected in an inlet opening at the feed end of the cylindrical drum which is rotated along a central longitudinal axis thereof. The shredded and ground organic waste material is mixed, further shredded and conveyed towards a rear end of the drum as the drum continuously rotates. The mixing and conveying is comprised by a plurality of vanes assemblies secured to an inner wall of the drum and spaced-apart from one another and rotatively driven with the drum. The organic waste material is discharged from the drum by suction.

BRIEF DESCRIPTION OF DRAWINGS

A preferred embodiment of the present invention will now be described with reference to the accompanying drawings in which:

FIG. 8 is a transverse end view inside the drum looking at the inlet end of the drum through a material mixing and conveying fane assembly;

FIG. 9A is a perspective view of a material mixing and conveying vane assembly;

FIG. 9B is a side view of FIG. 9A; and

DESCRIPTION OF PREFERRED EMBODIMENTS

Figure 1:
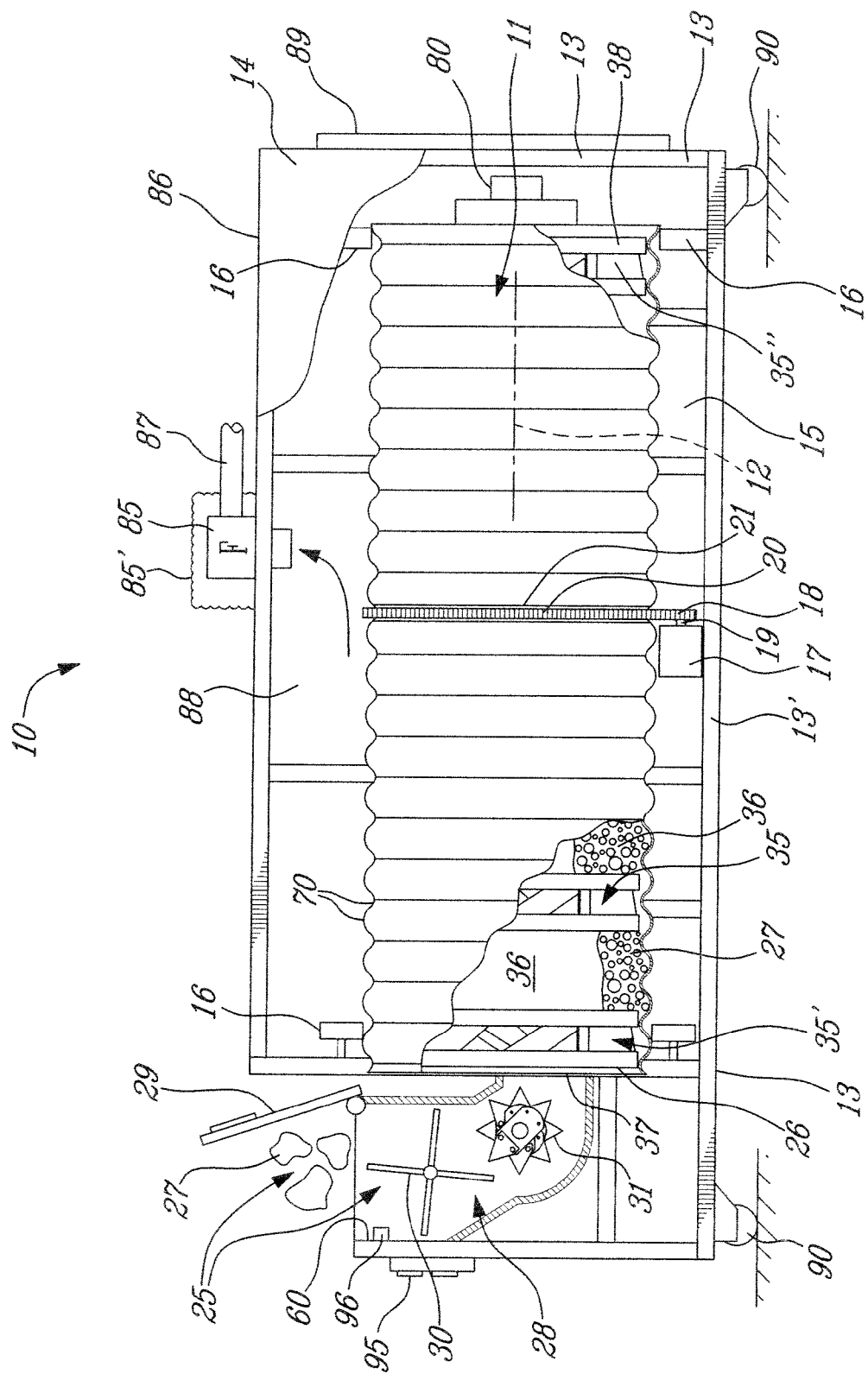
FIG. 1 is a simplified side view of the composting apparatus of the present invention shown partly fragmented and illustrating the basic component parts of the composting apparatus.
Figure 10:
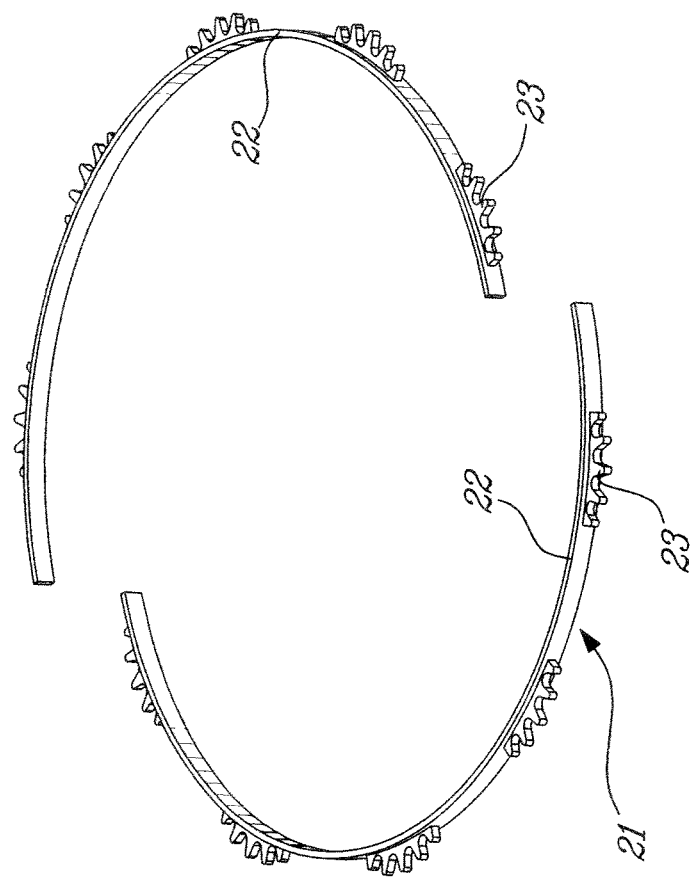
FIG. 10 is a perspective view showing the construction of the drive sprocket ring.

Referring now to the drawings and more particularly to FIG. 1, there is shown generally at 10 the composting apparatus of the present invention. The composting apparatus 10 comprises a cylindrical drum 11 rotatably supported along a central axis 12 thereof within a frame 13 which is provided with panels 14 to enclose the cylindrical drum 11. The panels 14 are removable from the frame 13 for access to the apparatus. The drum is rotatably and horizontally supported by large support rollers 15 secured to the bottom frame members 13' and guide wheels 16 disposed on both sides of the drum at the bottom and top of the drum. A drive motor 17 has a drive sprocket 18 secured to a drive shaft 19 thereof. The drive sprocket 18 is coupled to a drive link chain 20 which is in toothed engagement with a drive sprocket ring 21 secured about the drum. The drive sprocket ring 21 is illustrated in FIG. 10 and as hereinshown it consists of ring straps 22 provided with spaced-apart teeth sections 23 secured to the outer face of the ring straps 22 for engagement with the drive link chain 20.

As also shown in FIG. 1, a hopper 25 is secured at a feed end 26 of the drum 11 for receiving organic waste material 27 which may be in soft or hard form such as meat products or corn, bones, etc. Inside the hopper 25 there is provided a material shredding and grinding mechanism 28 which is rotatably secured in the hopper for shredding and grinding the organic waste material 27 and feeding it into an inlet opening 37 of the drum, as will be described later. A cover 29 is provided to close the upper end of the hopper when it is not necessary to place the organic waste material therein. A fan 85 prevents odors form escaping through the hopper.

The shredding and grinding mechanism 28 is herein comprised of a toothed feeder assembly 30 and a chopper assembly 31 which are intermeshed with one another and which will be described in detail later on.

As shown in FIG. 1, the inside of the drum 10 is provided with two or more material mixing and conveying vane assemblies 35 which are secured in a spaced-apart relationship inside the drum and rotatable therewith. The material mixing and conveying vane assemblies 35 define therebetween sub-composting compartments 36. As hereinshown, one of the material mixing and conveying vane assemblies 35' is positioned adjacent the inlet opening 37 whereby the threaded and ground material from the hopper is moved in the digestion chamber of the drum from the feed end 26 of the drum, where it is introduced, to the discharge end 38 as the drum continuously and slowly rotates.

Referring now to FIGS. 2 to 6, there will be described the construction and operation of the shredding and grinding mechanism 28. As shown in FIGS. 3A and 3B, the toothed feeder assembly 30 is provided by a steel tube or cylinder 38 on which is rigidly secured, herein by welding, a series of cutting teeth 39. These cutting teeth 39 are cut in plates 40, herein four plates welded longitudinally along the cylinder 38 and disposed along a transverse diametrical axis of the cylinder 38. The cylinder 38 is removably secured on a feeder shaft 41 which is hereinshown provided by two shaft sections provided with threaded bores 42 for receiving threaded bolts (not shown) extending through holes 43 provided in the cylinder 38. The cutting teeth 39 extend along the plates 40 all along the shaft 42 and these cutting teeth are of triangular shape having pointed ends 44 and troughs 45 formed therebetween whereby to permit passage of cutting blades of the chopper assembly 31 illustrated in FIGS. 4A and 4B. This construction permits ease of replacement of the cylinders 38 if the teeth become worn.

Figure 4A:
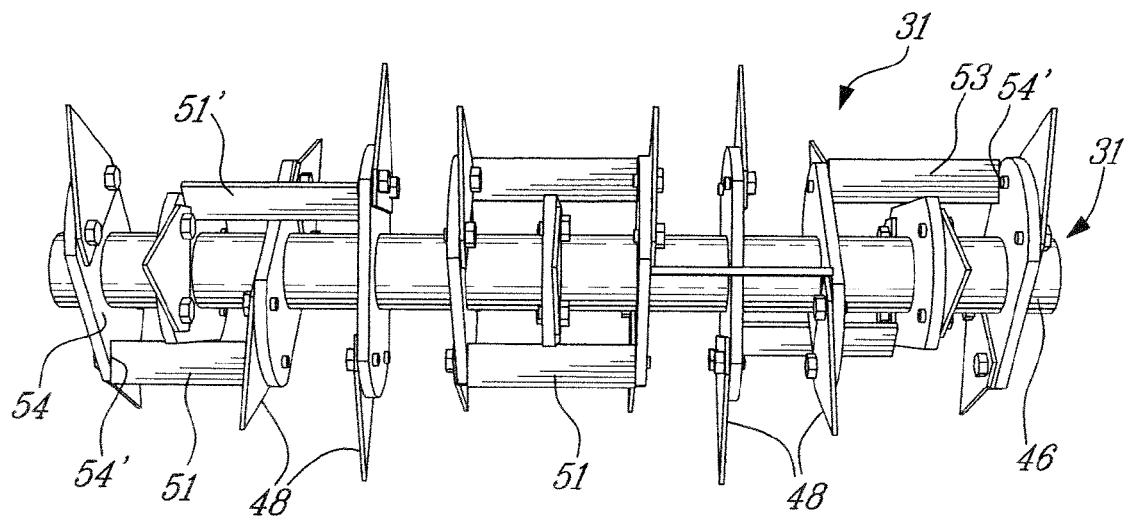
FIG. 4A is a side view of the chopper assembly herein showing the chopper cylinder with the knives and pusher plates secured thereto.
Figure 4B:
FIG. 4B is a side view of the chopper shaft on which the chopper cylinder is secured.
Figure 5:
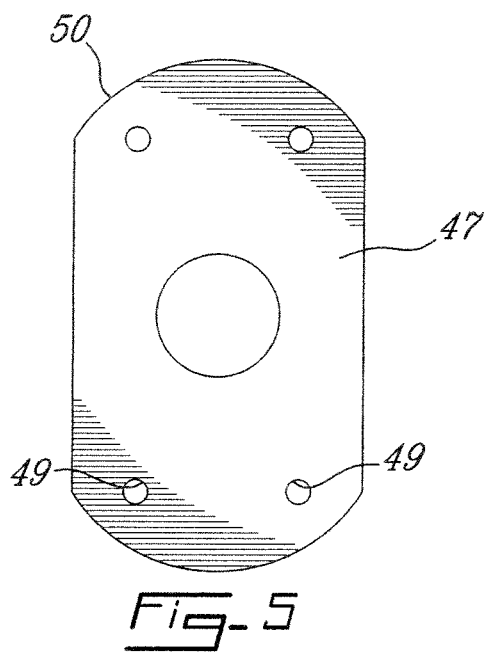
FIG. 5 is a plan view of the attachment plates secured to the chopper shaft cylinder.

As shown in FIG. 4A, the chopper assembly 31 also comprises a steel tube or cylinder 46 on which is welded a plurality of attachment plates 47, as better illustrated in FIG. 5, in spaced-apart relationship, herein about 2 inches apart and extending transversely thereto across the cylinder 46. Cutting blades 48 are removably secured to the attachment plates 47 at opposed ends of the plates through the attachment holes 49 provided in the plates as shown in FIG. 5. The outer ends of the plates have a convex edge 50. Pusher plates 51 are also secured through these attachment holes 49 between alternate ones of the attachment plates 47 and overlap, as shown in FIG. 4A and as illustrated by pusher plates 51 and 51'. These pusher plates are used to eject the shredded organic waste material into the inlet opening 37 of the drum 11. The cylinder 46 is secured to a chopper shaft 52 as shown in FIG. 4B and in a similar fashion as described with reference to the feeder assembly 30 illustrated in FIGS. 3A and 3B. Accordingly, it can be seen that the cutting blades 48 and pusher plates 51 can be easily replaced if damaged while the drum continues to rotate.

The pusher plates 51 are of simple construction and are comprised of a flat rectangular plate 53 having at opposed ends thereof transverse attachment flanges 54 provided with a hole therein for securement to one of the attachment holes 49 of the attachment plates 47. The pusher plates 51 are also oriented at an angle offset from adjacent attachment plates whereby to continuously eject shredded organic waste material into the inlet opening but in alternate fashion while the shaft rotates.

Figure 2:
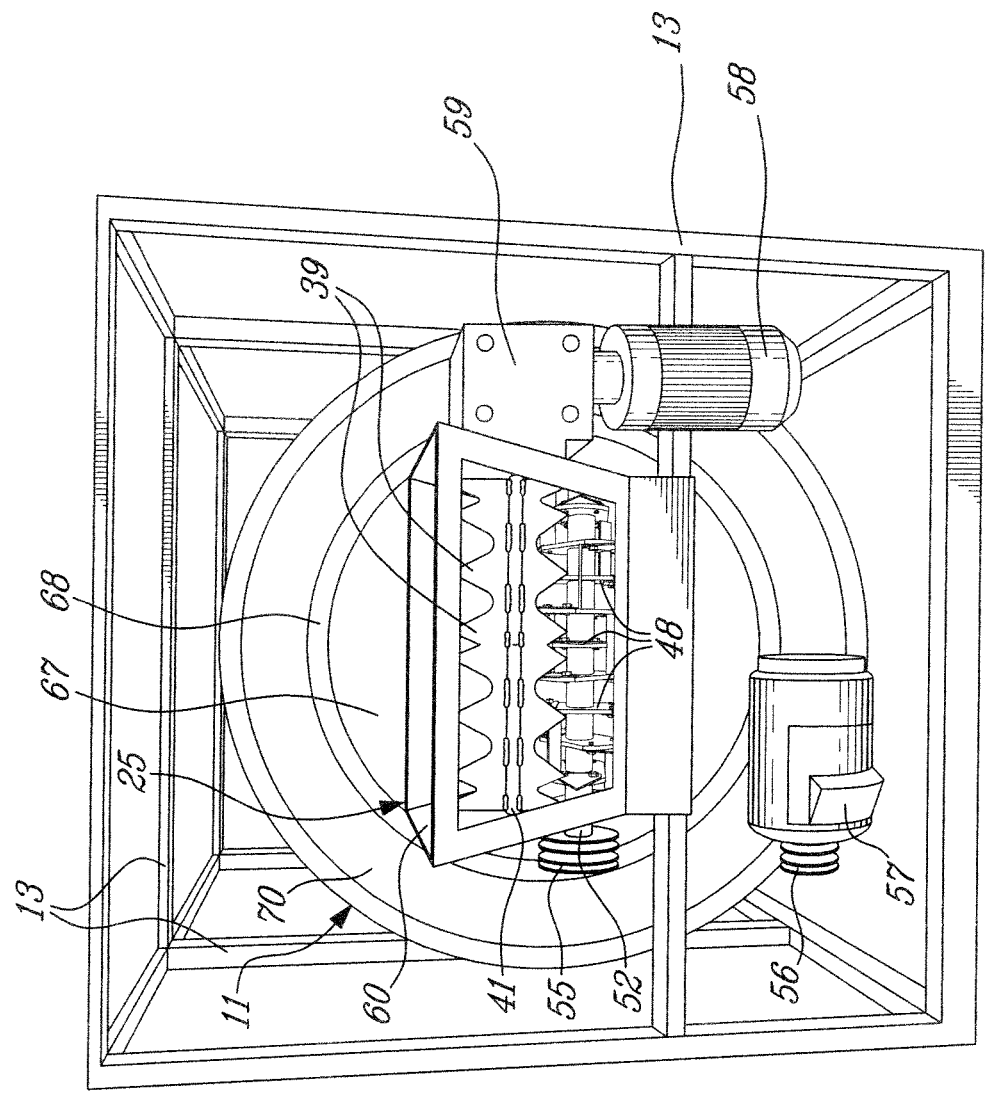
FIG. 2 is an end view of the composting apparatus with the panels removed and the rear inclined wall of the hopper removed showing the position of the material shredding and grinding mechanism.
Figure 3A:
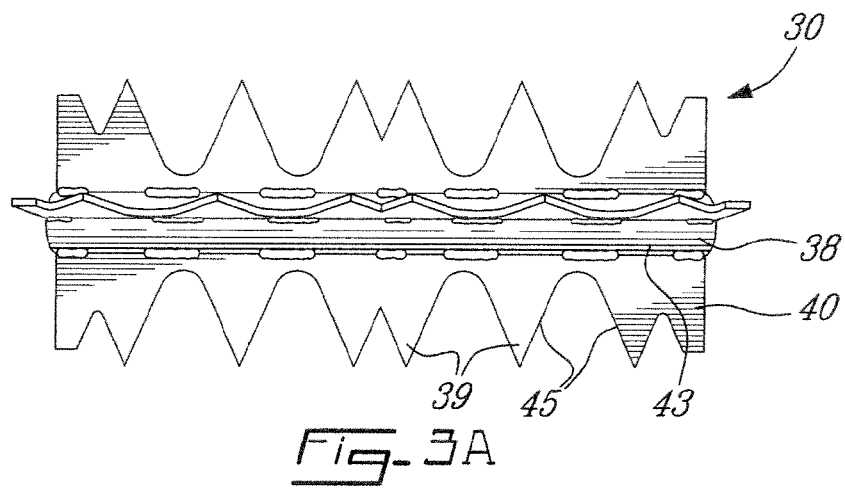
FIG. 3A is a side view of the toothed feeder shaft assembly, herein illustrating the toothed cylinder.
Figure 3B:
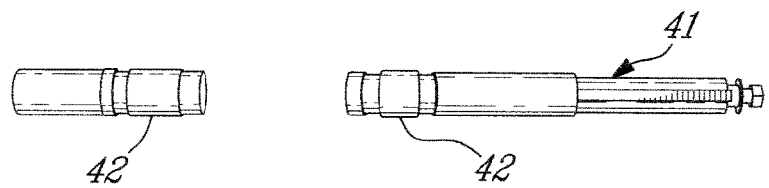
FIG. 3B is a side view of the feeder shaft about which the cylinder of FIG. 3A is secured.

With reference now to FIG. 2, it can be seen that the pointed teeth 39 are disposed to project between the cutting blades 48 of the chopper assembly 31. The chopper shaft 52 rotates in counter-rotation to the feeder shaft 41. The chopper shaft 52 is provided with a pulley 55 at a drive end of the shaft which is driven by a drive belt (not shown) coupled to the drive pulley 56 of an electric motor 57. The feeder shaft 41 is coupled to a further drive motor 58 through a gearing mechanism (not shown) secured in a gear box 59. The speed of rotation of the feeder shaft 41 and the chopper shaft 52 is set at a predetermined speed to provide effective shredding and chopping of any soft and hard organic waste material introduced in the hopper. The composting apparatus can take in meat, bones, fat, oils and grease to mention a few of such waste material. It is pointed out that the feeder shaft, the chopper shaft, and the drive sprocket of the drive motor 17 are synchronized with one another to prevent imbalance caused by vibration when these speeds are not synchronized. It is also pointed out that the toothed plates 40 instead of being secured on a cylinder 38 they could be welded directly on a feeder shaft. The same applies for the chopper assembly. However, by providing these assemblies in this fashion, it is simple, quick and efficient to provide repair of these assemblies as they can be easily substituted within short periods of time, thus providing easy servicing in the event of breakage or when eventually there is wear in the cutting blades.

Figure 6:
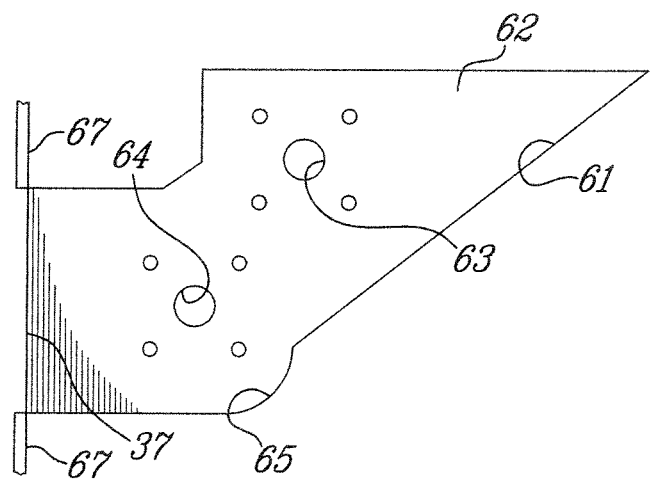
FIG. 6 is a plan view of a side wall of the hopper showing the relationship of the feeder shaft and the chopper shaft as well as the incline wall to direct waste material into the shredding and grinding mechanism.

As shown in FIGS. 1 and 6, the hopper 25 has an open top end 60 and an angulated bottom wall 61 defined between side walls 62. The side walls 62 are also provided with holes 63 and 64 to support therein the feeder shaft 41 and chopper shaft 52, respectively. Close to the bottom of the angulated bottom wall 61, there is provided an arcuate wall section 65 close to which are displaced the convex edges 50 of the attachment plates 47 of the chopper assembly 31 as well as the pusher plates 51 to eject the material from the bottom of the hopper into the inlet opening 37 as shown in FIG. 7A.

Figure 7A:
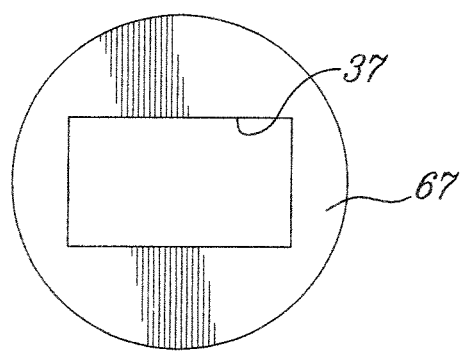
FIG. 7A is a plan view of the inlet opening disposed in a drum connecting circular plate.
Figure 7B:
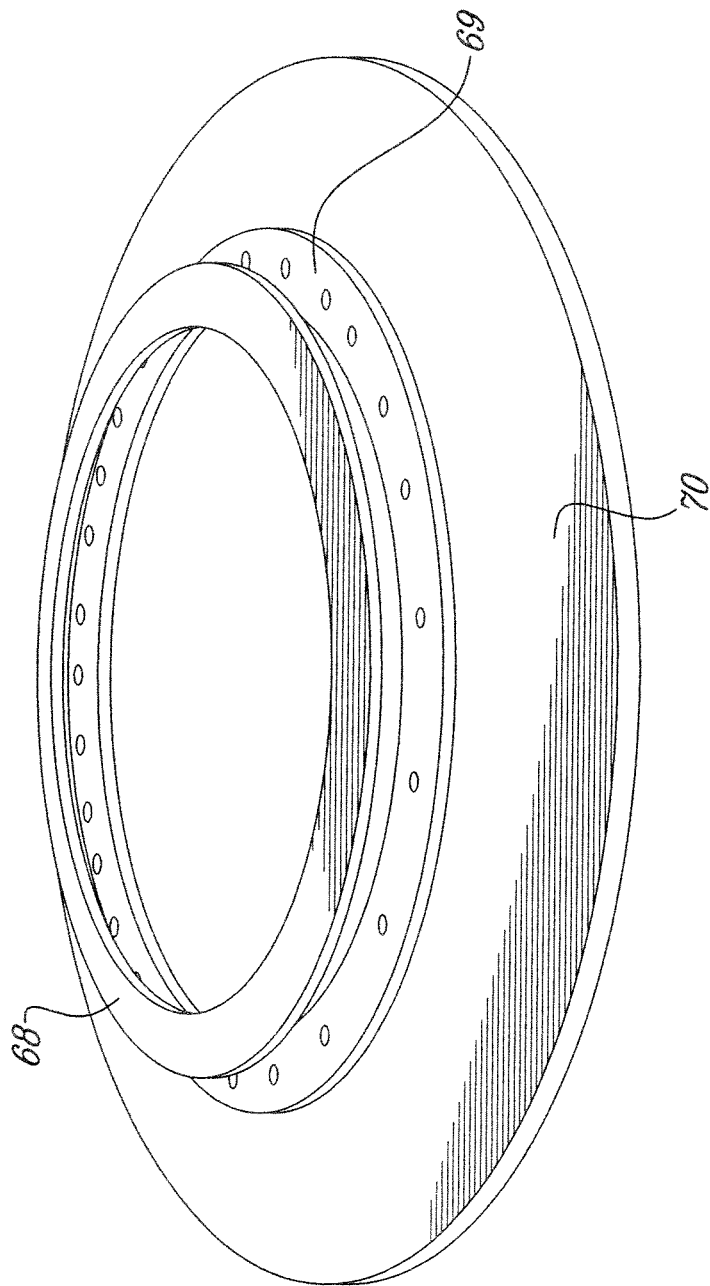
FIG. 7B is a perspective view of the sealing hub secured about the feed end of the drum together with a collar and friction ring in which the drum connecting circular plate of the hopper is held captive.

As shown in FIG. 7A, the inlet opening 37 is disposed substantially centrally in a drum connecting circular plate 67. This drum connecting circular plate 67 is held captive between a friction ring 68 and a collar 69 with the collar 69 secured to a sealing hub 70 which is immovably secured to the drum and rotates therewith. These component parts are illustrated in FIG. 7B. Accordingly, the drum connecting circular plate is substantially, sealingly engaged with the sealing hub at the feed end 26 of the cylindrical drum 11.

As shown in FIG. 1, the cylindrical drum 11 is constructed of recycled rubber material having a predetermined thickness and hardness and provided with an undulated side wall having valleys and troughs to provide stiffening ribs 70 integrally formed therealong. These valleys and troughs further improve the separation and remixing of the liquids contained in the organic material being mixed, further shredded and decomposing and composting in the drum as the drum rotates. The troughs collect liquids at the bottom of the drum and re-inject it into the solid material as the drum rotates. The drum is a non-corrosive leak-proof drum.

Referring now to FIGS. 8 to 9B, there is shown the construction of the material mixing and conveying vane assemblies 35. Each of the material mixing and conveying vane assemblies 35 is comprised of a cylindrical support herein formed by two circular steel bands 71 spaced-apart a predetermined distance by spacer bars 72 welded thereacross. The bands 71 are secured to the inner surface of the drum by bolts (not shown) provided with sealing gaskets or collars, well known in the art. As hereinshown, the vanes 73 are flat steel plates shaped to define opposed side edges 75 tapering inwardly towards a short free top edge 76. The vanes 73 have a wide securing bottom edge 74 spot-welded at 74' to opposed steel bands 71 and extend at an angle thereto to capture waste material from one side of the vane assemblies 35 and project it to the other side thereof conveying the waste material from the inlet end of the drum to the back discharge end 38.

The top edges 76 of the vanes are diagonally spaced-apart from one another to form a central opening 79 therebetween to oxygenate the waste material pushed therethrough by the vanes. The side edges 75 further cut and shred the material within the drum as it moves between the sub-composting compartments 36.

The discharge end 38 of the drum is provided with a suction line coupling 80 centrally of the drum to receive a suction hose from a transport vehicle (not shown). As the suction is applied, the drum is maintained in rotation at the same speed or higher speed controlled by the control panel 95 whereby material in the drum is conveyed towards the discharge end 38 of the drum towards the central opening of a rear conveying vane assembly 35" secured adjacent the suction coupling 80 to provide removal of the waste material in the drum. The organic waste material towards the discharge end of the drum is obviously composted more than the material at the feed end of the drum. However, the material is transported for further composting or for use in facilities to collect the gas generated by the compost and to use it for combustion and the production of electricity or for use in an aerobic digester to create gas to feed a gas grid for all sorts of uses. As shown in FIG. 1, a door 89 provides access to the suction line coupling.

The detachable panels 14 provide access to the composting apparatus for servicing and repair. A fan 85 is secured to the top wall 86 of the enclosure and has a filter to filter odor and is surrounded by insulation 85' for sound dampening. An exhaust flue 87 conducts the filtered odors from the interior 88 of the enclosure to atmosphere. The frame 13 is also mounted on wheels 90 for ease of displacement of the composting apparatus 10.

The control panel 95 is provided with switches and controls to place the composter in operation and to adjust the speed of the various motors depending on the size and application of the constructed composting apparatus. A sensor 96 is secured to the hopper to detect material fed into the hopper and feeds a signal to the control panel to automatically operate the material shredding and grinding mechanism for a predetermined period of time or cycle. The operating time of the shredding and grinding mechanism can also be used to predict the volume of material fed to the composter. The control panel provides local and remote signals indicative of the volume of waste material contained within the cylindrical drum 11 and the number of days in use after removal of its contents whereby to schedule the removal of the composted material in the composter.

Briefly summarizing the method of operation of the compositing apparatus, it comprises of feeding organic waste material 27 in a hopper 25 wherein the waste material is shredded and grounded by a combination of the toothed feeder assembly 30 which is provided with a series of cutting teeth which are intermeshed with a plurality of cutting blades secured to a chopper assembly 31. The feeder shaft and the chopper shaft are driven in counter-rotation. The chopper assembly is further provided with pusher plates 51 to push or eject the shredded and ground organic waste material in an inlet opening of the cylindrical drum which is rotated about its central longitudinal axis. The material is injected into a mixing and conveying vane assembly 35' which is disposed immediately adjacent the inlet opening which mixes and conveys the waste material towards the rear end of the drum 11 as the drum rotates. It is pointed out that the drum speed is adjustable to the desired use of the drum and this rotation causes the solid waste material and liquid material to mix with one another while being further shredded by the vanes of the mixing and conveying assemblies 35'. The undulations in the inner surface of the drum also favour mixing of the solids and liquids. The organic waste material is discharged from the drum by suction as previously described. Oxygen is admitted into the drum through the hopper which is not a sealed unit and the gases produced inside the cylindrical drum which escape into the interior 88 of the enclosure are evacuated by the fan 85 to atmosphere.

It is pointed out that the composting apparatus of the present invention is a self-contained, fully integrated unit which is easily displaceable and does not require a separate storage tank or crusher which are usually permanent installations and sometimes require installation or occupy space within a building. The composting apparatus of the present invention is easily displaceable and easy to install. As previously mentioned, it has several uses and may be made constructed of different sizes to accommodate, for example, residential building structures having several units or grocery stores, etc. The housing may also have its panels painted with decorative designs and colors to suit its location of use. Being a self-contained unit, it is also easily transportable to different sites.

It is within the ambit of the present invention to cover any obvious modifications of the embodiment described herewith provided such modifications fall within the scope of the appended claims.

I claim:

1. A composting apparatus for composting soft and hard organic material, said apparatus comprising a cylindrical drum rotatably supported along a central longitudinal axis thereof, drive means for rotating said drum about said longitudinal axis, a hopper at a feed end of said drum for receiving said organic waste material, a material shredding and grinding mechanism is rotatably secured in said hopper for shredding and grinding said organic waste material and feeding same to an inlet opening of said drum, said material shredding and grinding mechanism having a toothed feeder assembly provided with a series of cutting teeth rotatbly secured about a feeder shaft and extending longitudinally therealong, and a chopper assembly rolatably secured to a chopper shaft, a plurality of cutting blades disposed spaced-apart along said chopper shaft and extending transversely thereof to intermesh between said teeth of said feeder shaft, pusher plates extending transversly between said cutting blades to discharge material into said inlet opening, two or more material mixing and conveying vane assemblies secured in spaced-apart relationship in said drum and rotatable therewith, said material mixing and conveying vane assemblies defining sub-composting compartments therebetween, one of said material mixing and conveying vane assemblies being positioned adjacent said inlet opening, each said material mixing and conveying vane assemblies having a cylindrical support securable to an inner face of said drum and a plurality of vanes secured in spaced-apart relationship to said cylindrical support and projecting interiorly towards said central longitudinal axis and oriented at a common angle to mix and continue to shred and displace shredded and ground material from said inlet opening towards a rear end of said drum, means to vent said enclosure, and discharge means to discharge said material from said drum.

2. A composting apparatus as claimed in claim 1 wherein said chopper shaft is provided with a plurality of attachment plates immovably secured to said chopper shaft in spaced-apart relationship and extending transversely thereto across said chopper shaft, and a cutting blade removably secured to attachment means at a free end of each said attachment plates, said pusher plates being removably secured to said attachment means and extending therebetween in a top end portion thereof.

3. A composting apparatus as claimed in claim 2 wherein said pusher plates are rectangular flat plates having opposed securement end flanges, said pusher plates being oriented to have a side wall thereof disposed transverse to said attachment plates to project shredded and ground organic material into said inlet opening.

4. A composting apparatus as claimed in claim 2 wherein said attachment plates are oriented at an angle offset from adjacent attachment plates all about said chopper shaft, said pusher plates being secured between two attachment plates spanning an intermediate attachment plate whereby said pusher plates overlap one another in an offset relationship.

5. A composting apparatus as claimed in claim 1 wherein said toothed feeder shaft is provided with two or more series of pointed teeth formed in spaced-apart relationship along a tooth supporting steel plate welded along a steel cylinder secured about said feeder shaft, said pointed teeth defining a trough therebetween for the passage of said cutting blades of said chopper shaft.

6. A composting apparatus as claimed in claim 5 wherein there are four of said tooth supporting steel plates, said tooth supporting steel plates being secured to an elongated cylinder secured on opposed transverse diametrical axes of said cylinder.

7. A composting apparatus as claimed in claim 1 wherein said toothed feeder shaft is driven by a first motor, said chopper shaft being driven by a second motor, said drive means being a drive motor secured to a sprocket drive for rotating said drum, said first and second motors being operated in counter-rotation, said first and second motors and said drive motor being operated in synchronism.

8. A composting apparatus as claimed in claim 7 wherein said sprocket drive is comprised of a drive ring secured about said drum and having projecting teeth extending therefrom for toothed engagement with a drive link chain engaged by a drive sprocket secured to a drive shaft of said drive motor.

9. A composting apparatus as claimed in claim 1 wherein each said vane of said material mixing and conveying vane assemblies is comprised of a flat steel plate having inwardly tapering side edges, a wide securing bottom edge and a shorter free top edge, said free top edge of opposed vanes being diagonally spaced-apart from one another to form a central opening therebetween to oxygenate waste material, said side edges constituting cutting and shredding edges, there being a plurality of said material mixing and conveying vane assemblies secured in spaced relationship internally of said drum.

10. A composting apparatus as claimed in claim 1 wherein said inlet opening is disposed substantially centrally of said drum in a drum connecting circular plate of said hopper and a sealing hub secured about said feed end of said drum and rotatable therewith, a friction ring secured to said drum connecting wall and frictionally engaged with said drum connecting circular plate by a collar of said sealing hub to provide rotation of said hub about said drum connection circular plate.

11. A composting apparatus as claimed in claim 1 wherein said hopper has an open top end for receiving organic waste material therein, said hopper having an angulated bottom wall, opposed side walls and a drum connecting wall, said toothed feeder shaft being supported between said side walls above said angulated bottom wall, said chopper shaft being secured between said side walls below said feeder shaft adjacent a bottom end of said angulated bottom wall and in relation to a bottom arcuate wall section facing adjacent a bottom section of said inlet opening, said angulated bottom wall and arcuate wall section directing said shredded organic waste material into said grinding mechanism to eject the shredded organic waste into the inlet opening.

12. A composting apparatus as claimed in claim 1 wherein said cylindrical drum is constructed of rubber material and having an ondulated side wall forming stiffening ribs integrally formed therealong, said drum being a non-corrosive leak-proof drum, said drum being supported by rollers disposed on opposed sides thereof on a support frame.

13. A composting apparatus as claimed in claim 1 wherein said support frame is provided with detachable panels to provide access inside said enclosure, exhaust means to exhaust gas from said drum to the atmosphere, and access means for access to said rear end of said drum and said discharge means.

14. A composting apparatus as claimed in claim 13 wherein said discharge means is a suction line coupling provided at said rear end of said drum, said access means being a door for access to said suction line coupling.

\* \* \* \* \*